United States Patent
Perez et al.

(10) Patent No.: US 8,022,064 B2
(45) Date of Patent: Sep. 20, 2011

(54) PHENYLPENTADIENOYL DERIVATIVES AND THEIR USE AS PAR 1 ANTAGONISTS

(75) Inventors: Michel Perez, Castres (FR); Marie Lamothe, Castres (FR); Bruno Le Grand, Lautrec (FR); Robert Letienne, Castres (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 103 days.

(21) Appl. No.: 12/305,447

(22) PCT Filed: Jun. 19, 2007

(86) PCT No.: PCT/EP2007/056078
§ 371 (c)(1),
(2), (4) Date: Dec. 18, 2008

(87) PCT Pub. No.: WO2007/147822
PCT Pub. Date: Dec. 27, 2007

(65) Prior Publication Data
US 2010/0003260 A1 Jan. 7, 2010

(30) Foreign Application Priority Data
Jun. 19, 2006 (FR) .................. 06 05418

(51) Int. Cl.
*A61K 31/496* (2006.01)
*A61K 31/495* (2006.01)
*A61K 31/551* (2006.01)
*C07D 213/74* (2006.01)
*C07D 213/75* (2006.01)
*C07D 333/24* (2006.01)
*C07D 295/1851* (2006.01)

(52) U.S. Cl. ............... 514/218; 514/252.13; 514/253.01; 514/254.01; 514/255.01; 540/575; 544/360; 544/372; 544/379; 544/391

(58) Field of Classification Search .................. None
See application file for complete search history.

(56) References Cited

FOREIGN PATENT DOCUMENTS
| | | | |
|---|---|---|---|
| JP | 61-106564 A | | 5/1986 |
| JP | 61-137866 A | | 6/1986 |
| WO | 2008/155335 | * | 12/2008 |

OTHER PUBLICATIONS

Vippagunta et al Advanced Drug Delivery Reviews, vol. 48, pp. 3-26 (2001).*
Chackalamannil, S. et al., "Thrombin receptor (PAR-1) antagonists as novel antithrombotic agents", Expert Opinion on Therapeutic Patents 2006, United Kingdom, vol. 16, No. 4, pp. 493-505, 2006.
Vu et al., "Molecular cloning of a functional thrombin receptor reveals a novel proteolytic mechanism of receptor activation", Cell, vol. 64, pp. 1057-1068, 1991.
Coughlin et al., "Characterization of a functional thrombin receptor", J. Clin. Invest.. vol. 89, No. 2. pp. 351-355.1992.
O'Brien et al., "Thrombin responses in human endothelial cells", J. Biol. Chem., vol. 275, No. 18. pp. 13502-13509, 2000.
Hamilton et al., "Heterogeneous mechanisms of endothelium-dependent relaxation for thrombin and peptide activators of protease-activated receptor-1 in porcine isolated coronary artery", British Journal of Pharmacology, vol. 130, pp. 181-188, 2000.
Hung et al., "Thrombin-induced events in non-platelet cells are mediated by the unique proteolytic mechanism established for the cloned platelet thrombin receptor", Journal of Cell Biology. vol. 116, No. 3. pp. 827-832, 1992.
Vu et al., "Domains specifying thrombin-receptor interaction", Nature, vol. 353, pp. 674-677, 1991.
Ahn et al., "Nonpeptide thrombin receptor antagonists", Drug of the Future, vol. 26, No. 11, pp. 1065-1085, 2001.
Derian et al., "Blockage of the thrombin receptor protease-activated receptor-1 with a small-molecule antagonist prevents thrombus formation and vascular occlusion in nonhuman primates", Journal of Pharmacology and Experimental Therapeutics, vol. 304, No. 2, pp. 855-861, 2003.
Maryanoff et al., "Discovery of potent peptide-mimetic antagonists for the human thrombin receptor, protease-activated receptor-1 (PAR-1)", Curr. Med. Chem., Cardiovascular & Hematological Agents, vol. 1, pp. 13-36. 2003.
Steinberg, Susan F., "The cardiovascular actions of protease-activated receptors". Molecular Pharmacology, vol. 67, No. 1, pp. 2-11, 2005.
Moffatt et al., "Shooting for PARs in lung diseases", Current Opinion in Pharmacology,. vol. 4, pp. 221-229, 2004.

(Continued)

*Primary Examiner* — Emily Bernhardt
(74) *Attorney, Agent, or Firm* — Birch, Stewart, Kolasch & Birch, LLP

(57) ABSTRACT

The present invention relates to compounds of general formula (I): wherein: $R_1$ and $R_2$, identical or different, represent: an atom of hydrogen or halogen, CN or $NO_2$, with $R_1$ and $R_2$ not representing hydrogen simultaneously, m represents: 1 or 2 n represents: 0, 1 or 2 $R_3$ represents: phenyl substituted or not by one or more residues chosen among halogen, hydroxyl or $C_1$-$C_6$ alkyl; $C_2$-$C_6$ alkyl substituted or not by one or more residues chosen among halogen or hydroxyl; cycloalkyl; pyridine; thiophene; pyrrole substituted or not by $C_1$-$C_6$ alkyl; thiazole or furan; or the therapeutically-acceptable salts or solvates thereof.

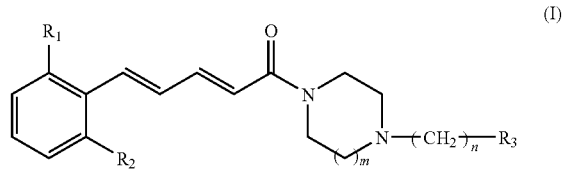

(I)

13 Claims, No Drawings

OTHER PUBLICATIONS

Vergnolle et al., "A role for proteinase-activated receptor-1 in inflammatory bowel diseases". Journal of Clinical Investigation, vol. 114, No. 10, pp. 1444-1456, 2004.

Fiorucci et al., "$PAR_1$ antagonism protects against experimental liver fibrosis. Role of proteinase receptors in stellate cell activation", Hepatology, vol. 39, pp. 365-375, 2004.

Even-Ram et al., "Thrombin receptor overexpression in malignant and physiological invasion processes", Nature Medicine, vol. 4, No. 8, pp. 909-914, 1998.

Boire et al., "PAR1 is a matrix metalloprotease-1 receptor that promotes invasion and tumorigenesis of breast cancer cells", Cell, vol. 120, pp. 303-313, 2005.

Schechter et al., "Reaction of mast cell protease tryptase and chymase with protease activated receptors (PARs) on keratinocytes and fibroblasts". Journal of Cellular Physiology, vol. 176. pp. 365-373, 1998.

Algermissen et al., "Distribution and potential biologic function of the thrombin receptor PAR-1 on human keratinocytes", Arch. Dermatol. Res., vol. 292, pp. 488-495, 2000.

Meyer-Hoffert et al., "Trypsin induces epidermal proliferation and inflammation in murine skin", Experimental Dermatology vol. 13 pp. 234-241, 2004.

Ossovskaya et al., "Protease-activated receptors: contribution to physiology and disease", Physiol. Rev., vol. 84, pp. 579-621, 2004.

Arunlakshana et al., "Some quantitative uses of drug antagonists", Brit. J. Pharmacol., vol. 14, pp. 48-58, 1959.

* cited by examiner

PHENYLPENTADIENOYL DERIVATIVES AND THEIR USE AS PAR 1 ANTAGONISTS

The present invention relates to phenylpentadienoyl derivatives, a method of manufacturing same, pharmaceutical compositions comprised of same and the use of same as drugs for the treatment and/or prevention of arterial and venous thrombosis, acute coronary syndromes, restenosis, stable angina, heart rhythm disorders, myocardial infarction, hypertension, heart failure, stroke, inflammatory disorders, pulmonary diseases, gastrointestinal diseases, fibrosis development in chronic liver disease patients, cancer and skin diseases. The present invention also relates to combinations of the inventive compounds with other cardiovascular agents.

Thrombosis is regarded as a primary factor in vascular occlusion, which is the cause of a number of pathophysiological complications. Antithrombotic therapy is thus extremely important as it can reduce the risk of cardiovascular mortality and coronary events. Although several types of molecules have shown effective antithrombotic activity in man, there remains a need for novel molecules that provide advantages compared to existing compounds, some of which have a negative impact on bleeding time or are accompanied by other undesirable side effects (such as, for example, the risk of ulcer with aspirin).

Protease-activated receptor-1 (PAR-1) was recently cloned (Vu et al., Cell, 1991, 64: 1057-1068) and its mechanism of action elucidated (Coughlin et al., J. Clin. Invest. 1992, 89(2): 351-355). This receptor, notably present on the surface of platelets but also on the surface of endothelial cells (O'Brien et al., J. Biol. Chem. 2000, 275: 13502-13509), smooth muscle cells (Hamilton et al., Br. J. Pharmacol. 2000, 130: 181-188) and fibroblasts (Hung et al., J. Cell. Biol. 1992, 116(3): 827-832), is activated by thrombin and thus is also called thrombin receptor. The N-terminus of the protein is cleaved by thrombin between arginine 41 and serine 42 to free a new end which will act, after folding upon the active site, as a receptor agonist (Vu et al., Nature, 1991, 353, 674-677). With respect to platelets, this specific PAR-1 receptor activation mechanism leads to thrombin-mediated platelet aggregation.

The blocking of this activation, for example with PAR-1 receptor antagonists, can inhibit thrombin-mediated platelet aggregation (Ahn et al., Drug of the Future, 2001, 26: 1065-1085). The blocking of these receptors can thus lead to the treatment or prevention of thrombosis (Derian et al., J. Pharmacol. Exp. Ther., 2003, 855-861), acute coronary syndromes (Ossovskaya et al., Physiol. Rev., 2004, 84: 579-621) and restenosis (Maryanoff et al., Curr. Med. Chem. Cardiovasc. Hematol. Agents., 2003, 13-36) and can reduce myocardial necroses during infarction or reperfusion (Steinberg et al., Mol. Pharmacol. 2005, 67: 2-11). At the pulmonary level, PAR-1 antagonist activity can prevent certain inflammatory diseases (Moffatt et al., Curr. Op. Pharmacol., 2004, 221-229). At the gastrointestinal level, PAR-1 receptor antagonist activity can prevent certain inflammatory diseases (Vergnolle et al., J. Clin. Invest., 2004, 1444-1456). PAR-1 antagonists can also be of use in the treatment of fibroses in patients with chronic liver disease (Fiorucci et al., Hepatology, 2004, 39: 365-375). They can also be of use as anti-cancer agents given that they act to control cellular proliferation and metastases (Evan-Ram et al., Nat. Med., 1998, 909-914; Boire et al., Cell., 2005, 120: 303-313). Lastly, PAR-1 antagonists can be of interest in dermatology to treat certain skin diseases (Schechter et al., J. Cell. Physiol., 1998, 176:365-373; Algermissen et al., Arch. Dermatol. Res., 2000, 292:488-495; Meyer-Hoffert et al., Exp. Dermatol., 2004, 13: 234-241).

The present invention relates to a novel class of PAR-1 antagonists that are distinguished from the prior art by their different chemical structure and their remarkable biological property.

Compounds of the present invention are of general formula (I):

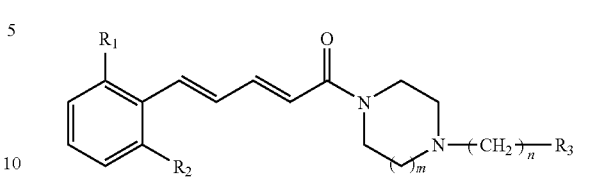

wherein:
$R_1$ and $R_2$, identical or different, represent:
   an atom of hydrogen or halogen, CN or $NO_2$, with $R_1$ and $R_2$ not representing hydrogen simultaneously,
m represents:
   1 or 2
n represents:
   0, 1 or 2
$R_3$ represents:
   phenyl substituted or not by one or more residues chosen among halogen, hydroxyl or $C_1$-$C_6$ alkyl; $C_2$-$C_6$ alkyl substituted or not by one or more residues chosen among halogen or hydroxyl; cycloalkyl; pyridine; thiophene; pyrrole substituted or not by $C_1$-$C_6$ alkyl; thiazole or furan;
or the therapeutically-acceptable salts or solvates thereof.

In the preceding definitions:
All combinations of substituents or variables are possible insofar as they lead to stable compounds.
The term "halogen" represents fluorine, chlorine, bromine or iodine.
The term "alkyl" represents linear or branched, saturated or unsaturated aliphatic hydrocarbon chains comprising the specified number of carbon atoms.
The term "cycloalkyl" represents cyclic hydrocarbon chains comprising 3 to 10 carbon atoms.
Therapeutically-acceptable salts of compounds of the present invention include conventional nontoxic salts of compounds of the invention such as those formed from organic or inorganic acids. As an example, the following can be cited: inorganic acid salts such as hydrochloric, hydrobromic, phosphoric and sulfuric acids, as well as organic acid salts such as acetic, trifluoroacetic, propionic, succinic, fumaric, malic, tartaric, citric, ascorbic, maleic, glutamic, benzoic, salicylic, toluenesulfonic, methanesulfonic, stearic and lactic acids.
These salts can be synthesized from compounds of the invention containing a base moiety and corresponding acids according to conventional chemical methods.
Therapeutically-acceptable solvates of compounds of the present invention include conventional solvates such as those formed during the final preparation step of compounds of the invention as a result of the presence of solvents. Solvates due to the presence of water or ethanol can be cited as an example.

Among the compounds of general formula (I) according to the present invention, one particularly advantageous class of compounds are compounds of general formula (I) wherein $R_1$ is nitro, $R_2$ is hydrogen, m equals 1, n equals 0 and $R_3$ is phenyl substituted by one or more halogens or $C_1$-$C_6$ alkyls, cycloalkyl or pyridine.

Among the compounds of general formula (I) according to the present invention, a second particularly advantageous class of compounds corresponds to compounds of general formula (I) wherein $R_1$ is cyano, $R_2$ is hydrogen, m equals 1, n equals 0 and $R_3$ is phenyl substituted by one or more halogens or $C_1$-$C_6$ alkyls, cycloalkyl or pyridine.

The present invention also relates to the preparation of compounds of general formula (I) by the general methods described in the following synthesis diagrams supplemented by, as the case may be, any standard technique described in the literature, known to those persons skilled in the art, or presented in the experiments section.

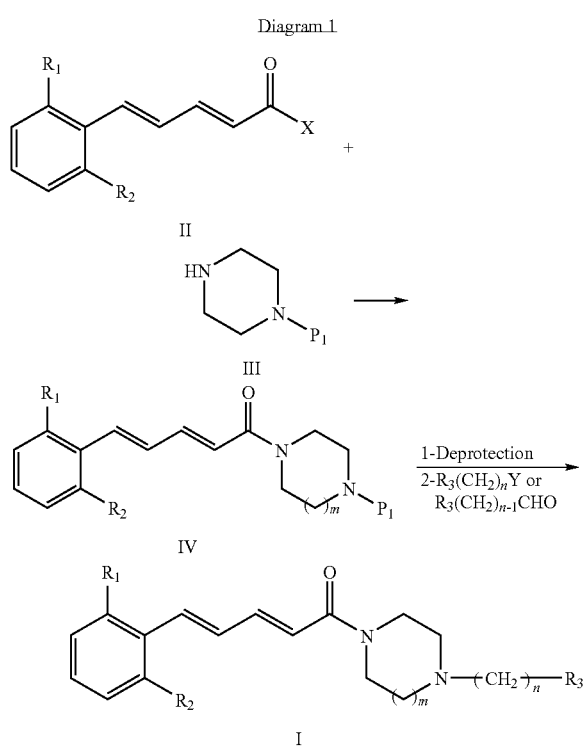

Diagram 1 illustrates the first general method that can be used for the preparation of compounds of general formula (I). In the general formulas above, $R_1$, $R_2$ and $R_3$ are defined as in the preceding description of general formula (I). In diagram 1 above, however, n represents 1 or 2 only, $P_1$ represents a protective group and X can represent a group such as chlorine or hydroxyl. The starting compound, of general formula (II), can be prepared by methods and techniques known to those persons skilled in the art. A particularly advantageous method consists of reacting benzyl halide with triphenylphosphine in a polar solvent such as DMF or DMSO at a temperature between 20° C. and 100° C. to form phosphonium salt. Phosphonium salt can then be deprotonated using a base such as NaH, for example, in a solvent such as DMF or THF at a temperature between −20° C. and 40° C. and then reacting with an α,β-unsaturated aldehyde carrying an ester such as, for example, ethyl (2E)-4-oxobut-2-enoate. The ester obtained (mixture of Z/E and E/E isomers) is first isomerized by treatment with iodine in a polar solvent such as acetonitrile to yield the E/E isomer exclusively, and then saponified by treatment with a mineral base such as KOH, NaOH or LiOH in a polar solvent such as water, ethanol or THF at a temperature between 20° C. and 100° C., yielding compounds (II) in which X would thus be hydroxyl. A second particularly advantageous method consists of reacting an aromatic aldehyde with a phosphonate such as ethyl 4-(diethoxyphosphoryl)but-2-enoate in the presence of a base such as, for example, NaH, $Cs_2CO_3$ or $K_2CO_3$ in a solvent such as THF, dichloromethane or dichloroethane at a temperature between −20° C. and 100° C. The ester obtained (mixture of Z/E and E/E isomers) is first isomerized by treatment with iodine in a polar solvent such as acetonitrile, yielding the E/E isomer exclusively, and then saponified by treatment with a mineral base such as KOH, NaOH or LiOH in a polar solvent such as water, ethanol or THF at a temperature between 20° C. and 100° C., yielding compounds (II) in which X would thus be hydroxyl. A third particularly advantageous method consists of reacting an aromatic α,β-unsaturated aldehyde with ethyl (diethoxyphosphoryl)acetate in the presence of a base such as, for example, NaH, $Cs_2CO_3$ or $K_2CO_3$ in a solvent such as THF, dichloromethane or dichloroethane at a temperature between −20° C. and 100°°C. The ester obtained can be saponified by treatment with a mineral base such as KOH, NaOH or LiOH in a solvent such as water, ethanol or THF at a temperature between 20° C. and 100° C., yielding compounds (II) in which X would thus be hydroxyl. A fourth particularly advantageous method consists of reacting an aromatic carrying a halogen, such as bromine or iodine, with an (E)-penta-2,4-dienoyl ester, such as methyl or ethyl (E)-penta-2,4-dienoate ester, in the presence of a palladium catalyst such as palladium acetate, a phosphine such as tri-o-tolylphosphine or tri-phenylphosphine in the presence of a base such as, for example, $Et_3N$ or $iPr_2NEt$, in an open or sealed reactor, without a solvent or with a solvent such as DMF, DMSO or DMA at a temperature between 20° C. and 120° C. The ester thus obtained (primarily the E/E isomer) can be saponified by treatment with a mineral base such as KOH, NaOH or LiOH in a solvent such as water, ethanol or THF at a temperature between 20° C. and 100° C., yielding compounds (II) in which X would thus be hydroxyl. In this case the first step is a condensation reaction between the carboxylic acid (II) and the amine (III). This reaction can be carried out by methods and techniques known to those persons skilled in the art. A particularly advantageous method consists of reacting these two entities in the presence of 1-(3-dimethylaminopropyl)-3-ethyl-carbodiimide (EDC), 3-hydroxy-1,2,3-benzotriazin-4(3H)-one, and a tertiary amine such as diisopropylethylamine in a polar aprotic solvent, such as dichloromethane, at a temperature between −15° C. and 40° C. The carboxylic acid can also be transformed into acid chloride (X then corresponds to chlorine) by treatment with a reagent such as thionyl chloride at a temperature between 20° C. and 100° C. In this case the first step consists of the reaction between an acid chloride and an amine. This reaction can be carried out by methods and techniques known to those persons skilled in the art. A particularly advantageous method consists of reacting the two entities in the presence of an organic or inorganic base such as, for example, $Et_3N$, $iPr_2NEt$, pyridine, NaH, $Cs_2CO_3$ or $K_2CO_3$ in a solvent such as THF, dichloromethane, DMF or DMSO at a temperature between −20° and 100° C.

After deprotection of the intermediate (IV) by methods and techniques known to those skilled in the art ("Protective Groups in Organic Synthesis," T. W. Greene, John Wiley & Sons, 1981 and "Protecting Groups," P. J. Kocienski, Thieme Verlag, 1994), the intermediate obtained can react with a reagent of formula $R_3(CH_2)_nY$, wherein Y represents a leaving group such as, for example, Cl, Br, I, $OSO_2CH_3$, $OSO_2CF_3$ or O-tosyl. In this case, the reaction will be carried out in the presence of an organic or inorganic base such as, for example, $Et_3N$, $iPr_2NEt$, NaH, $Cs_2CO_3$ or $K_2CO_3$ capable of being supported on a resin such as PS-DIEA or MP-carbonate, in a polar anhydrous solvent such as dichloromethane, THF, DMF or DMSO at a temperature between −20° and 100° C. Another preparation method consists of carrying out a reducing amination reaction using an aldehyde of formula $R_3$—$(CH_2)_{n-1}$—CHO in which $R_3$ and n are as defined previously, with the deprotected amine of general formula (IV) and a reducing agent such as $NaBH_4$, $NaBH_3CN$ or $NaBH(OAc)_3$ capable of being supported on a resin such as MP—$BH_3CN$, in a polar solvent such as 1,2-dichloroethane, dichloromethane, THF, DMF or MeOH, at a pH that can be controlled by the addition of an acid such as acetic acid, at a temperature between −20° C. and 100° C.

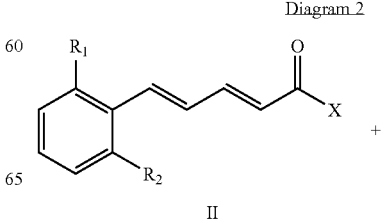

-continued

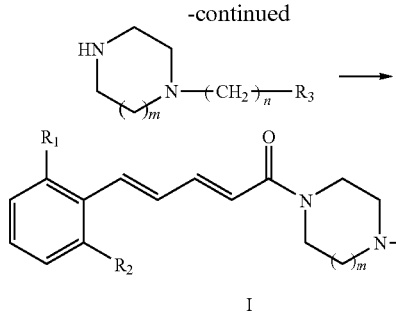

Diagram 2 illustrates the second general method that can be used for the preparation of compounds of general formula (I). In the general formulas above, $R_1$, $R_2$, $R_3$ and n are defined as in the description of general formula (I). X can represent a group such as chlorine or hydroxyl. The starting compound, of general formula (II), can be prepared by methods and techniques known to those persons skilled in the art, in particular those described above. In the case in which X is chlorine, synthesis consists of the reaction between an acid chloride and an amine. This reaction can be carried out by methods and techniques known to those persons skilled in the art. A particularly advantageous method consists of reacting the two entities in the presence of an organic or inorganic base such as, for example, $Et_3N$, $iPr_2NEt$, pyridine, NaH, $Cs_2CO_3$ or $K_2CO_3$ in a solvent such as THF, dichloromethane, DMF or DMSO at a temperature between −20° and 100° C.

In the case in which X is hydroxyl, synthesis consists of condensation between the carboxylic acid (II) and the amine (V). The reaction can be carried out by methods and techniques known to those persons skilled in the art. A particularly advantageous method consists of condensing a carboxylic acid of general formula (II) with an amine of general formula (III) in the presence of 1-(3-dimethylaminopropyl)-3-ethyl-carbodiimide (EDC), 3-hydroxy-1,2,3-benzotriazin-4(3H)-one and a tertiary amine such as diisopropylethylamine, in a polar aprotic solvent such as dichloromethane, at a temperature between −15° C. and 40° C.

When it is desired to isolate a compound of general formula (I) containing at least one base function in salt state by the addition of an acid, such a result can be achieved by treating the free base of general formula (I) (in which at least one base function is present) with a suitable acid, preferably in an equivalent quantity.

The examples which follow illustrate the invention without limiting its scope in any way.

EXAMPLE 1

2[5-Oxo-5-(4-pyridin-2-yl-piperazin-1-yl)-penta-1,3-dienyl]-benzonitrile

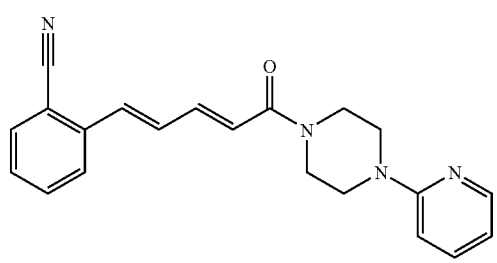

EXAMPLE 1A

Ethyl 5-(2-cyano-phenyl)-penta-2,4-dienoate

2-Bromomethyl-benzonitrile (3 g, 15.3 mmol) in solution in DMF (50 ml) at 80° C. is treated with triphenylphosphine (4.42 g, 16.83 mmol). After 3 hours of agitation, the mixture is returned to room temperature and sodium hydride (60% in oil) (673 mg, 16.83 mmol) and ethyl 4-oxo-but-2-enoate (2.16 g, 16.83 mmol) are added. After 16 hours of agitation at room temperature, the mixture is evaporated to dryness, taken up in ethyl acetate and washed with water. The organic phase is dried on $Na_2SO_4$, filtered and evaporated to dryness. The syrup obtained is purified by silica column chromatography and eluted with a 9/1 EDP/AcOEt mixture. Product 1A is isolated in the form of a yellow syrup (2.73 g, 71%) of E/E and Z/E isomers.

Mass spectrum (ESI+): m/z 228 (M+H$^+$)

EXAMPLE 1B

Ethyl (2E,4E)-5(2-cyano-phenyl)-penta-2,4-dienoate

Compound 1A (2.34 g, 10.3 mmol) in solution in acetonitrile (14 ml) is treated at room temperature with iodine (15.0 mg, 0.06 mmol). After 3 hours of agitation the mixture is evaporated to dryness, taken up in dichloromethane and washed with a $Na_2SO_3$ solution (0.01 M). The organic phase is dried on $Na_2SO_4$, filtered and evaporated to dryness. Product 1B is isolated in the form of a solid (2.26 g, 97%) and is used as-is for the following step.

$^1$H NMR, DMSO-d$_6$ (ppm): 1.25 (t, 3H); 4.16 (q, 2H); 6.21 (d, 1H); 7.34 (m, 2H); 7.50 (m, 2H); 7.74 (t, 1H); 7.87 (d, 1H); 7.96 (d, 1H).

EXAMPLE 1C 5-(2-Cyano-phenyl)-penta-2,4-dienoic acid

Compound 1B (2.0 g, 8.82 mmol) in solution in ethanol (50 ml) is treated with 1 N potash (13.2 ml, 13.2 mmol). After 1.5 hours of agitation at reflux, the mixture is evaporated to dryness, taken up with water and treated with 1 N HCl up to acid pH. The precipitate formed is filtered, washed with water and dried under a vacuum to yield pure product 1C (1.63 g, 93%).

Mass spectrum (ESI−): m/z 198 (M−H$^−$)

EXAMPLE 1

2-[5-Oxo-5-(4-pyridin-2-yl-piperazin-1-yl)-penta-1,3-dienyl]-benzonitrile

Acid 1C (700 mg, 3.51 mmol) in solution in dichloromethane (10 ml) in the presence of diisopropylethylamine (DIEA) (1.2 ml, 7.02 mmol) is treated, at room temperature, with 1-(3-dimethylaminopropyl)-3-ethylcarbodiimide (EDCI) hydrochloride (807 mg, 4.21 mmol), 3-hydroxy-1,2,3-benzotriazin-4(3H)-one (HOOBT) (686 mg, 4.21 mmol) and then 1-pyridin-2-yl-piperazine (642 µl, 4.21 mmol). After 16 hours of agitation the reaction mixture is diluted with dichloromethane and washed with 1 N soda and water. The organic phase is dried on $MgSO_4$, filtered and evaporated to dryness. The syrup obtained is purified by silica column chromatography and eluted with a ½ petroleum ether/AcOEt mixture. Product 1 is isolated in the form of a yellow solid (910 mg, 75%). This product is taken up in ethyl acetate then salified by the addition of a solution of HCl in ether to yield the corresponding hydrochloride in the form of a yellow solid (1.04 g).

$^1$H NMR, DMSO-d6 (ppm): 3.81 (broad s, 8H); 6.94 (m, 2H); 7.18 (m, 1H); 7.38 (m, 3H); 7.51 (t, 1H); 7.74 (t, 1H); 7.86 (d, 1H); 7.91 (d, 1H); 7.96 (t, 1H); 8.06 (d, 1H).

Mass spectrum (ESI+): m/z 345 (M+H$^+$)

EXAMPLE 2 TO 8

Compounds 2 to 8 were synthesized from intermediate 1C and corresponding amines according to the conditions described for the preparation of compound 1.

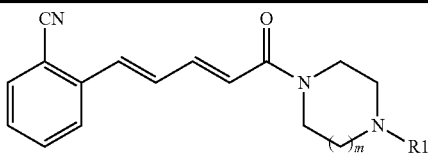

| Example | m | R1 | Compound name | Mass spectrum (M + H)$^+$ |
|---|---|---|---|---|
| 2 | 1 | Cyclopentyl | 2-[5-(4-Cyclopentyl-piperazin-1-yl)-5-oxo-penta-1,3-dienyl]-benzonitrile | 336 |
| 3 | 1 | Cyclohexyl | 2-[-5-(4-Cyclohexyl-piperazin-1-yl)-5-oxo-penta-1,3-dienyl]-benzonitrile | 350 |
| 4 | 1 | 3-Cl-propyl | 2-{5-[4-(3-Chloro-propyl)-piperazin-1-yl]-5-oxo-penta-1,3-dienyl}-benzonitrile | 344 |
| 5 | 1 | 3-Cl-phenyl | 2-{5-[4-(3-Chloro-phenyl)-piperazin-1-yl]-5-oxo-penta-1,3-dienyl}-benzonitrile | 378 |
| 6 | 1 | 2-OH-phenyl | 2-{5-[4-(2-Hydroxy-phenyl)-piperazin-1-yl]-5-oxo-penta-1,3-dienyl}-benzonitrile | 360 |
| 7 | 2 | 2,4-diMe-benzyl | 2-{5-[4-(2,4-Dimethyl-benzyl)-[1,4]diazepan-1-yl]-5-oxo-penta-1,3-dienyl}-benzonitrile | 400 |
| 8 | 2 | 2-Me-benzyl | 2-{5-[4-(2-Methyl-benzyl)-[1,4]diazepan-1-yl]-5-oxo-penta-1,3-dienyl}-benzonitrile | 386 |

EXAMPLE 9

5-(2-Chloro-phenyl)-1-(4-cyclopentyl-piperazin-1-yl)-penta-2,4-dien-1-one

EXAMPLE 9A

Ethyl 5-(2-chloro-phenyl)-penta-2,4-dienoate

Ethyl 4-(diethoxy-phosphoryl)-but-2-enoate (3.92 g, 15.65 mmol) in solution in THF (70 ml) at 0° C. is treated with sodium hydride (60% in oil) (630 mg, 15.7 mmol). After 30 minutes of agitation at 0° C., 2-chloro-benzaldehyde (2.0 g, 14.22 mmol) is added and the mixture is agitated from 0° C. to room temperature for 16 hours. The mixture is then evaporated to dryness, taken up in AcOEt and washed with water. The organic phase is dried on MgSO4, filtered and evaporated to dryness. The syrup obtained is purified by silica column chromatography and eluted with a 2/1 EDP/CH$_2$Cl$_2$ mixture. Product 9A is isolated in the form of a yellow oil (1.1 g, 33%).

EXAMPLE 9B 5-(2-Chloro-phenyl)-penta-2,4-dienoic acid

Compound 9A (2.1 g, 8.87 mmol) in solution in THF (20 ml) is treated with a 1 N LiOH solution (35 ml, 35.4 mmol). After 2 hours of agitation at room temperature and 1 hour at reflux, the mixture is evaporated to dryness, taken up with water and treated with 4 N HCl up to acid pH. The precipitate formed is filtered, washed with water and then dried under a vacuum to yield pure product 9B (1.70 g, 92%).

Mass spectrum (ESI–): m/z 207 (M–H$^-$)

EXAMPLE 9

5-(2-Chloro-phenyl)-1-(4-cyclopentyl-piperazin-1-yl)-penta-2,4-dien-1-one

Compound 9 is prepared from intermediate 9B (67.0 mg, 0.32 mmol) and cyclopentylpiperazine (101.3 mg, 0.45 mmol) according to the conditions described for the preparation of compound 1 from 1C. The pure product is isolated in the form of hydrochloride (99 mg, 81%).

Mass spectrum (ESI+): m/z 345 (M+H$^+$)

EXAMPLES 10 TO 15

Compounds 10 to 15 were synthesized from intermediate 9B and corresponding amines according to the conditions described for the preparation of compound 1 from 1C.

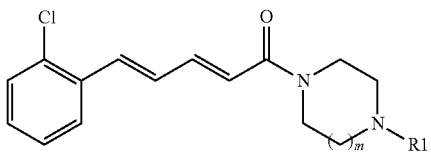

| Example | m | R1 | Compound name | Mass spectrum (M + H)+ |
|---|---|---|---|---|
| 10 | 1 | Cyclohexyl | 5-(2-Chloro-phenyl)-1-(4-cyclohexyl-piperazin-1-yl)-penta-2,4-dien-1-one | 359 |
| 11 | 1 | Cycloheptyl | 5-(2-Chlorophenyl)-1-(4-cycloheptyl-piperazin-1-yl)-penta-2,4-dien-1-one | 373 |
| 12 | 1 | 3-Cl-propyl | 5-(2-Chloro-phenyl)-1-[4-(3-chloro-propyl)-piperazin-1-yl]penta-2,4-dien-1-one | 353 |
| 13 | 1 | 2-Pyridine | 5-(2-Chloro-phenyl)-1-(4-pyridin-2-yl-piperazin-1-yl)-penta-2,4-dien-1-one | 354 |
| 14 | 2 | 2-Me-benzyl | 5-(2-Chloro-phenyl)-1-[4-(2-methyl-benzyl)-[1,4]diazepan-1-yl]-penta-2,4-dien-1-one | 395 |
| 15 | 2 | 2F-benzyl | 5-(2-Chloro-phenyl)-1-[4-(2-fluoro benzyl)-[1,4]diazepan-1-yl]-penta-2,4-dien-1-one | 399 |

EXAMPLE 16

5-(2-Nitro-phenyl)-1-(4-phenyl-piperazin-1-yl)-penta-2,4-dien-1-one

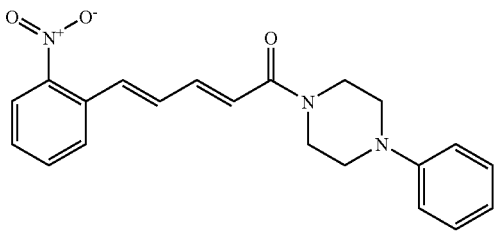

EXAMPLE 16A

Ethyl 5-(2-nitro-phenyl)-penta-2,4-dienoate 3-(2-Nitro-phenyl)-propenal (4.0 g, 22.5 mmol) in solution in toluene (67 ml) is treated with ethyl (triphenylphosphoranyl)-acetate (8.25 g, 23.7 mmol). After 2 days of agitation at reflux, the mixture is evaporated to dryness, purified by silica column chromatography and eluted with a 2/1 EDP/AcOEt mixture. Product 16A is isolated in the form of a yellow solid (4.96 g, 90%).

$^1$H NMR, DMSO-$d_6$ (ppm): 1.24 (t, 3H); 4.16 (q, 2H); 6.19 (d, 1H); 7.17 (dd, 1H); 7.35 (d, 1H); 7.45 (dd, 1H); 7.59 (t, 1H); 7.77 (t, 1H); 7.89 (d, 1H); 8.00 (d, 1H).

Mass spectrum (ESI+): m/z 248 (M+H$^+$)

EXAMPLE 16B 5-(2-Nitro-phenyl)-penta-2,4-dienoic acid

Intermediate 16A (2.59 g, 10.5 mmol) is saponified according to the conditions described for the preparation of compound 1C from 1B. The pure product is isolated in the form of a white solid (2.27 g, 99%).

Mass spectrum (ESI–): m/z 218 (M–H$^-$)

EXAMPLE 16

5-(2-Nitro-phenyl)-1-(4-phenyl-piperazin-1-yl)-penta-2,4-dien-1-one

Compound 16 is prepared from intermediate 16B (404 mg, 1.84 mmol) and phenyl-piperazine (415 µl, 2.20 mmol) according to the conditions described for the preparation of compound 1 from 1C. The pure product is isolated in the form of hydrochloride (621 mg, 87%).

$^1$H NMR, DMSO-$d_6$ (ppm): 3.29 (broad s, 4H); 3.82 (broad s, 4H); 6.94 (d, 1H); 7.00 (t, 1H); 7.20 (m, 4H); 7.32 (m, 3H); 7.57 (t, 1H); 7.75 (t, 1H); 7.87 (d, 1H); 7.99 (d, 1H).

Mass spectrum (ESI+): m/z 364 (M+H$^+$)

EXAMPLES 17 TO 26

Compounds 17 to 26 were synthesized from the intermediate 16B and corresponding amines according to the conditions described for the preparation of compound 1 from 1C.

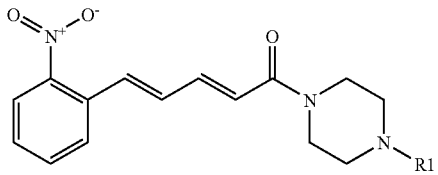

| Example | R1 | Compound name | Mass spectrum (M + H)+ |
|---|---|---|---|
| 17 | Cyclohexyl | 1-(4-Cyclohexyl-piperazin-1-yl)-5-(2-nitro-phenyl)-penta-2,4-dien-1-one | 370 |
| 18 | Cyclopentyl | 1-(4-Cyclopentyl-piperazin-1-yl)-5-(2-nitro-phenyl)-penta-2,4-dien-1-one | 356 |
| 19 | 4-F-phenyl | 1-[4-(4-Fluoro-phenyl)-piperazin-1-yl]-5-(2-nitro-phenyl)-penta-2,4-dien-1-one | 382 |
| 20 | 3-Cl-propyl | 1-[4-(3-Chloro-propyl)-piperazin-1-yl]-5-(2-nitro-phenyl)-penta-2,4-dien-1-one | 364 |
| 21 | 2-pyridine | 5-(2-Nitro-phenyl)-1-(4-pyridin-2-yl-piperazin-1-yl)-penta-2,4-dien-1-one | 365 |

-continued

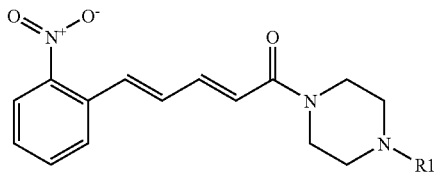

| Example | R1 | Compound name | Mass spectrum (M + H)+ |
| --- | --- | --- | --- |
| 22 | Cyclopentyl-methyl | 1-(4-Cyclopentylmethyl-piperazin-1-yl)-5-(2-nitro-phenyl)-penta-2,4-dien-1-one | 370 |
| 23 | Thiophene-3-methyl | 5-(2-Nitro-phenyl)-1-(4-thiophen-3-ylmethyl-piperazin-1-yl)-penta-2,4-dien-1-one | 384 |
| 24 | 4-F-benzyl | 1-[4-(4-Fluoro-benzyl)-piperazin-1-yl]-5-(2-nitro-phenyl)-penta-2,4-dien-1-one | 396 |
| 25 | Butyl | 1-(4-Butyl-piperazin-1-yl)-5-(2-nitro-phenyl)-penta-2,4-dien-1-one | 344 |
| 26 | 3-Cl-phenyl | 1-[4-(3-Chloro-phenyl)-piperazin-1-yl]-5-(2-nitro-phenyl)-penta-2,4-dien-1-one | 398 |

EXAMPLE 27

5-(2,6-Difluoro-phenyl)-1-(4-phenyl-piperazin-1-yl)-penta-2,4-dien-1-one

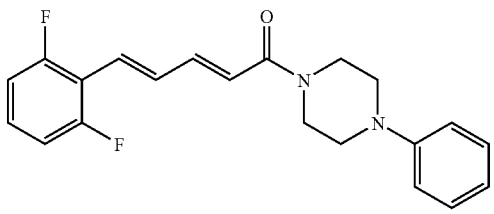

EXAMPLE 27A

Ethyl 5-(2,6-difluoro-phenyl)-penta-2,4-dienoate

Ethyl (diethoxy-phosphoryl)-acetate (3.72 ml, 18.7 mmol) in solution in THF (114 ml) is treated with sodium hydride (60% in oil) (819 mg, 20.4 mmol) at room temperature for 5 minutes. 3-(2,6-Difluoro-phenyl)-propenal (2.87 g, 17.0 mmol) in solution in THF (29 ml) is then added dropwise. After 3 hours of agitation at room temperature, the mixture is evaporated to dryness, taken up in ethyl acetate and washed with water. The organic phase is dried on Na₂SO₄, filtered and evaporated to dryness. The yellow solid obtained is used directly in the following reaction.

EXAMPLE 27B 5-(2,6-Difluoro-phenyl)-penta-2,4-dienoic acid

Intermediate 27B (3.28 g, 13.76 mmol) is saponified according to the conditions described for the preparation of compound 1C from 1B. The pure product is isolated in the form of a beige solid (2.56 g, 88%).
Mass spectrum (ESI−): m/z 209 (M−H⁻)

EXAMPLE 27

5-(2,6-Difluoro-phenyl)-1-(4-phenyl-piperazin-1-yl)-penta-2,4-dien-1-one

Compound 27 is prepared from intermediate 27B (60 mg, 0.285 mmol) and phenyl-piperazine (68.1 μl, 0.342 mmol) according to the conditions described for the preparation of compound 1 from 1C. The pure product is isolated in the form of beige powder (72 mg, 79%).
Mass spectrum (ESI+): m/z 355 (M+H⁺)

EXAMPLES 28 TO 31

Compounds 28 to 31 were synthesized from intermediate 27B and corresponding amines according to the conditions described for the preparation of compound 1 from 1C.

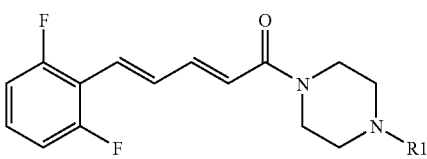

| Example | R1 | Compound name | Mass spectrum (M + H)+ |
| --- | --- | --- | --- |
| 28 | Cyclohexyl | 1-(4-Cyclohexyl-piperazin-1-yl)-5-(2,6-difluoro-phenyl)-penta-2,4-dien-1-one | 361 |
| 29 | 3-Cl-propyl | 1-[4-(3-Chloro-propyl)-piperazin-1-yl]-5-(2,6-difluoro-phenyl)-penta-2,4-dien-1-one | 355 |

-continued

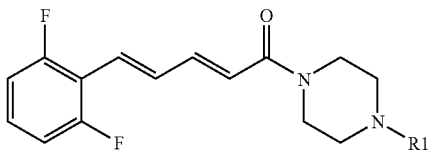

| Example | R1 | Compound name | Mass spectrum (M + H)+ |
|---|---|---|---|
| 30 | Cyclopentyl | 1-(4-Cyclopentyl-piperazin-1-yl)-5-(2,6-difluoro-phenyl)-penta-2,4-dien-1-one | 347 |
| 31 | 4-F-benzyl | 5-(2,6-Difluoro-phenyl)-1-[4-(4-fluoro-benzyl)-piperazin-1-yl]-penta-2,4-dien-1-one | 387 |

EXAMPLE 32

1-(4-Cyclopentyl-piperazin-1-yl)-5-(2-fluoro-phenyl)-penta-2,4-dien-1-one

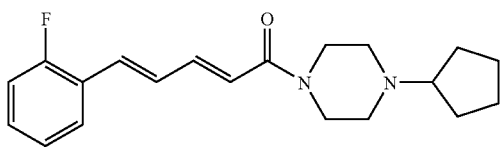

EXAMPLE 32A

Ethyl 5-(2-fluoro-phenyl)-penta-2,4-dienoate

Intermediate 32A is prepared from 3-(2-difluoro-phenyl)-propenal and ethyl(diethoxy-phosphoryl)-acetate according to the conditions described for the preparation of compound 27A.
Mass spectrum (ESI+): m/z 221 (M+H+)

EXAMPLE 32B 5-(2-Fluoro-phenyl)-penta-2,4-dienoic acid

Intermediate 32B is prepared from compound 32A according to the conditions described for the preparation of compound 27B.
Mass spectrum (ESI−): m/z 191 (M−H)

EXAMPLE 32

1-(4-Cyclopentyl-piperazin-1-yl)-5-(2-fluoro-phenyl)-penta-2,4-dien-1-one

Compound 32 is prepared from intermediate 32B (100.0 mg, 0.52 mmol) and cyclopentyl-piperazine (165.3 mg, 0.73 mmol) according to the conditions described for the preparation of compound 1 from 1C. The pure product is isolated in the form of white powder (122 mg, 64%).
Mass spectrum (ESI+): m/z 329 (M+H+)

EXAMPLES 33 TO 36

Compounds 33 to 36 were synthesized from intermediate 32B and corresponding amines according to the conditions described for the preparation of compound 1 from 1C.

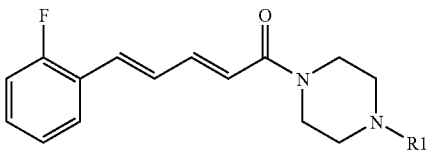

| Example | R1 | Compound name | Mass spectrum (M + H)+ |
|---|---|---|---|
| 33 | Cyclohexyl | 1-(4-Cyclohexyl-piperazin-1-yl)-5-(2-fluoro-phenyl)-penta-2,4-dien-1-one | 343 |
| 34 | 2-Pyridine | 5-(2-Fluoro-phenyl)-1-(4-pyridin-2-yl-piperazin-1-yl)-penta-2,4-dien-1-one | 338 |
| 35 | Phenyl | 5-(2-Fluoro-phenyl)-1-(4-phenyl-piperazin-1-yl)-penta-2,4-dien-1-one | 337 |
| 36 | 3-Cl-propyl | 1-[4-(3-Chloro-propyl)-piperazin-1-yl]-5-(2-fluoro-phenyl)-penta-2,4-dien-1-one | 337 |

The derivatives of the present invention are PAR-1 receptor antagonists as the results of the models described below demonstrate:

In a variety of cell types, activation of PAR-1 receptors by the SFLLR peptide (a selective PAR-1 agonist) triggers an intracellular signal cascade leading to the release of calcium by the endoplasmic reticulum. Chinese hamster ovarian (CHO) cells constituently express PAR-1 receptor. In this cell line, the release of calcium consecutive to receptor activation by SFLLR is measured by a fluorometry technique (fluorometric imaging plate reader, or FLIPR) using a selective probe for calcium (Fluo-3AM). The emission of fluorescence is pharmacologically proportional to the efficiency of the PAR-1 agonist and to its concentration. The compounds described in the present invention have demonstrated that they are capable of antagonizing PAR-1 receptors and thus decreasing the release of calcium induced by the agonist.

Materials:

Culture medium: Ham's F-12 (Ham, R. G., Proc. Nat. Acad. Sci. 1965, 53: 288) supplemented with 10% fetal calf serum and antibiotic (Probenicid, 2.5 mM).

Fluorescent probe: Fluo-3AM (4 µM; Teflabs, Austin, Tex., USA)

Agonist: SFLLR-$NH_2$ (Serine, phenylalanine, leucine, leucine, arginine).

Methods: CHO cells are inoculated in 96-well plates (60,000 cells per well) in the presence of 200 µl of culture medium for 24 hours. The cells are incubated with the calcium fluorescent probe for 1 hour at 37° C. The cells are then washed 10 minutes before the signal is measured. PAR-1 antagonist is then injected (0.01 µM to 10 µM). The plates are placed in the FLIPR (Molecular Devices, UK) to measure calcium fluorescence at two wavelengths (488 nm and 540 nm: Sullivan et al., Calcium Signaling Protocols 1999, 125-136). Measurements are taken for 5 min before the antagonist is added and for 10 min following its administration. Maximum fluorescence minus baseline fluorescence is measured in 4 different wells. The test is carried out in duplicate. Under these conditions, the derivatives of the present invention were identified as PAR-1 receptor antagonists (antagonism >60% of the calcium signal at 10 µM). The dose-response curves (0.01 µM to 32 µM) obtained with the SFLLR agonist allowed determination of the effective concentration inducing 50% of the maximum effect ($EC_{50}$). The strengths (pA2) of some of the PAR-1 antagonists described in the present invention were calculated using the method of Arunlakshana and Schild (Brit. J. Pharmacol., 1959, 14: 48-58) from the $EC_{50}$ shifts observed at three concentrations.

Results:

The several examples which follow, chosen among the compounds of the present invention, illustrate the completely unexpected capacity of these compounds to antagonize PAR-1 receptors.

| Example | pA2 |
| --- | --- |
| 1 | 6.5 |
| 2 | 6.63 |
| 9 | 6.64 |
| 16 | 7.23 |
| 18 | 7.16 |
| 21 | 7.11 |

The in vivo antiplatelet aggregation and antithrombotic activities of PAR-1 antagonists have been shown in a guinea pig model of arterial thrombosis, which has very high hemodynamic shear stress. In a vascular bed, an endothelial lesion causes the intravascular formation of a platelet-rich thrombus that will gradually occlude all of the vessel's lumen. The platelet aggregation process is strongly activated by thrombin via PAR-1 receptors. The compounds described in the present invention have demonstrated that they are capable of antagonizing PAR-1 receptors and thus delaying thrombus formation.

Materials:

The studies are conducted using guinea pigs (PAR-1 receptors similar to man). Irradiation by means of a green laser light in the presence of a photosensitizing agent (Rose Bengal administered intravenously) damages the carotid endothelium. The carotid flow rate is quantified using a Transonic flow probe. The time required to completely occlude the carotid (flow rate of 0) is measured.

Methods:

After the animal is anesthetized (60 mg/kg pentobarbital), 5 mm of the carotid artery is resected and the laser is placed 4 mm above the artery. A flow probe placed upstream measures occlusion time. Rose Bengal (20 mg/kg) is administered by intravenous route and the vessel is irradiated at a wavelength of 514 nm (for 3 min). PAR-1 antagonists are administered by intravenous route using a bolus (over 2 min immediately before administration of Rose Bengal) followed by a 15-minute perfusion which begins when the laser is turned on.

Results:

Certain compounds described in the present invention have shown that they are able, after administration by intravenous route at doses from 0.16 mg/kg to 2.5 mg/kg, to delay the time before the formation of a thrombus from 10% to 90% compared to animals receiving vehicle alone.

The derivatives according to the invention are also of use in the treatment of atrial fibrillation.

In the case of postinfarction cardiac-cavity volume overload, the right and left auricles dilate, thus constituting the substrate for the genesis of atrial fibrillation. The disturbance of hemostasis in the cavity of the dilated auricle of a patient suffering from atrial fibrillation leads to an abnormal concentration of thrombin. The inventors have demonstrated that this accumulation of thrombin is responsible for an up-regulation of PAR-1 which can trigger the proliferation of fibroblasts as well as the formation of platelet thrombus.

By their mechanism of action, PAR-1 antagonists can thus prevent atrial dilation, fibroblast proliferation and thrombus formation in the auricle of a patient suffering from atrial fibrillation.

As a result, a PAR-1 antagonist constitutes an effective preventative and/or curative treatment for atrial fibrillation. The compounds described in the present invention have demonstrated that they are capable of antagonizing PAR-1 receptors and preventing auricle dilation.

Materials:

The studies are carried out using male rats. Because they tolerate surgery best, rats in a weight range of 180-200 g on arrival were chosen for the experiment. Measurements of the various myocardial cavities are conducted by echocardiography on the anesthetized animal.

Methods:

The animal is anesthetized by a 3.5% mixture of isoflurane in oxygen (Aerrane, Baxter Laboratories). A thoracotomy perpendicular to the sternum of approximately 2 cm is performed at the level of the fourth intercostal space towards the left forefoot. A ligature (4-0 silk, CC1 needle, Ethicon) is passed around the left coronary artery 1 mm from its origin. A surgical knot, sufficiently tight to completely occlude the vessel, is tied around the left coronary artery. The continuously-recording electrocardiogram makes it possible to verify the satisfactory positioning of the ligature. Two months after the procedure, the animals are again anesthetized for an echocardiographic measurement of the cardiac cavities and a measurement of blood velocity within the myocardium using pulsed Doppler. Lastly, the animals are euthanized by sodium pentobarbital overdose (160 mg/kg, IP) for various histological measurements. The animals are force-fed daily PAR-1 antagonist products from 24 h after infarction until the animal is sacrificed.

Results:

Certain compounds described in the present invention have shown that they are able, after administration by oral route in doses from 10-100 mg/kg/d for 60 days, to reduce by 20% to 90% the auricle surface (measured by echocardiography) compared to untreated animals.

The present invention also relates to pharmaceutical compositions containing as an active ingredient a compound of general formula (I), or a pharmaceutically-acceptable salt thereof, mixed or combined with a suitable excipient. Such compositions can assume the form, for example, of solid or liquid compositions, emulsions, lotions or creams.

As solid compositions for oral administration, tablets, pills, powders (in gelatin capsules or in packets) or granules can be used. In such compositions, the active ingredient according to the invention is mixed with one or more inert diluents, such as starch, cellulose, sucrose, lactose or silica, under an argon flow. Such compositions may also include substances other than diluents, for example one or more lubricants such as magnesium stearate or talc, a colorant, a coating (for sugar-coated pills) or a varnish.

As liquid compositions for oral administration, the following can be used: pharmaceutically-acceptable solutions, suspensions, emulsions, syrups and elixirs containing inert diluents such as water, ethanol, glycerol, vegetable oils or liquid paraffin. Such compositions can include substances other than diluents, for example wetting, sweetening, thickening, flavoring or stabilizing agents.

Sterile compositions for parenteral administration can be, preferably, aqueous or non-aqueous solutions, suspensions or emulsions. As a solvent or vehicle, the following can be used: water, propylene glycol, polyethylene glycol, vegetable oils, in particular olive oil, injectable organic esters, for example ethyl oleate or other suitable organic solvents. Such compositions can also contain additives, in particular wetting agents, isotonic agents, emulsifiers, dispersants and stabilizers. Sterilization can be achieved in several ways, for example by sterilizing filtration, by incorporating sterilizing agents in the composition, by irradiation or by heating. Such compositions can also be prepared in the form of sterile solid compositions that can be dissolved in sterile water or in any other injectable sterile medium just before use.

Compositions for rectal administration are suppositories or rectal capsules that contain, in addition to the active product, excipients such as cocoa butter, semi-synthetic glycerides or polyethylene glycols.

Compositions for topical administration can be creams, lotions, eye drops, mouth washes, nose drops or aerosols, for example.

Doses depend on desired effect, treatment duration and administration route, and are generally between 0.001 g and 1 g (preferably between 0.005 g and 0.75 g) per day, preferably by oral route for an adult, with unit doses ranging from 0.1 mg to 500 mg of active substance.

Generally, the doctor will establish suitable dosing according to the patient's age, weight and other specific factors of the case.

According to a specific embodiment, the present invention also relates to products containing a compound according to general formula (I) and another cardiovascular agent as a combination product for simultaneous, separate or time-release use in cardiovascular therapy, the other cardiovascular agent able to be an antiplatelet agent such as aspirin, clopidogrel, ticlopidine, abciximab, tirofiban or eptifibatide.

The invention claimed is:
1. Compounds of general formula (I):

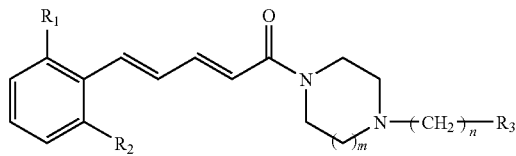

wherein:
$R_1$ and $R_2$, identical or different, represent:
an atom of hydrogen or halogen, CN or $NO_2$, with $R_1$ and $R_2$ not representing hydrogen simultaneously,
m represents:
1 or 2
n represents:
0, 1 or 2
$R_3$ represents:
phenyl substituted or not by one or more residues chosen among halogen, hydroxyl or $C_1$-$C_6$ alkyl; $C_2$-$C_6$ alkyl substituted or not by one or more residues chosen among halogen or hydroxyl; cycloalkyl; pyridine; thiophene; pyrrole substituted or not by $C_1$-$C_6$ alkyl; thiazole or furan; or the therapeutically-acceptable salts thereof.

2. Compounds according to claim 1, wherein $R_1$ is nitro, $R_2$ is hydrogen, m equals 1, n equals 0 and $R_3$ is phenyl substituted by one or more halogens or $C_1$-$C_6$ alkyls, cycloalkyl or pyridine.

3. Compounds according to claim 1, wherein $R_1$ is cyano, $R_2$ is hydrogen, m equals 1, n equals 0 and $R_3$ is phenyl substituted by one or more halogens or $C_1$-$C_6$ alkyls, cycloalkyl or pyridine.

4. A compound according to claim 1 selected among:
2-[5-Oxo-5-(4-pyridin-2-yl-piperazin-1-yl)-penta-1,3-dienyl]-benzonitrile;
2-[5-(4-Cyclopentyl-piperazin-1-yl)-5-oxo-penta-1,3-dienyl]-benzonitrile;
2-[5-(4-Cyclohexyl-piperazin-1-yl)-5-oxo-penta-1,3-dienyl]-benzonitrile;
2-{5-[4-(3-Chloro-propyl)-piperazin-1-yl]-5-oxo-penta-1,3-dienyl}-benzonitrile;
2-{5-[4-(3-Chloro-phenyl)-piperazin-1-yl]-5-oxo-penta-1,3-dienyl}-benzonitrile;
2-{5-[4-(2-Hydroxy-phenyl)-piperazin-1-yl]-5-oxo-penta-1,3-dienyl}-benzonitrile;
2-{5-[4-(2,4-Dimethyl-benzyl)-[1,4]diazepan-1-y1]-5-oxo-penta-1,3-dienyl}-benzonitrile;
2-{5-[4-(2-Methyl-benzyl)-[1,4]diazepan-1-yl]-5-oxo-penta-1,3-dienyl}-benzonitrile;
5-(2-Chloro-phenyl)-1-(4-cyclopentyl-piperazin-1-yl)-penta-2,4-dien-1-one;
5-(2-Chloro-phenyl)-1-(4-cyclohexyl-piperazin-1-yl)-penta-2,4-dien-1-one;
5-(2-Chloro-phenyl)-1-(4-cycloheptyl-piperazin-1-yl)-penta-2,4-dien-1-one;
5-(2-Chloro-phenyl)-1-[4-(3-chloro-propyl)-piperazin-1-yl]-penta-2,4-dien-1-one;
5-(2-Chloro-phenyl)-1-(4-pyridin-2-yl-piperazin-1-yl)-penta-2,4-dien-1-one;
5-(2-Chloro-phenyl)-1-[4-(2-methyl-benzyl)-[1,4]diazepan-1-yl]-penta-2,4-dien-1-one;
5-(2-Chloro-phenyl)-1-[4-(2-fluoro-benzyl)-[1,4]diazepan-1-yl]-penta-2,4-dien-1-one;
5-(2-Nitro-phenyl)-1-(4-phenyl-piperazin-1-yl)-penta-2,4-dien-1-one;
1-(4-Cyclohexyl-piperazin-1-yl)-5-(2-nitro-phenyl)-penta-2,4-dien-1-one;
1-(4-Cyclopentyl-piperazin-1-yl)-5-(2-nitro-phenyl)-penta-2,4 dien-1-one;

1-[4-(4-Fluoro-phenyl)-piperazin-1-yl]-5-(2-nitro-phenyl)-penta-2,4 dien-1-one;
1-[4-(3-Chloro-propyl)-piperazin-1-yl]-5-(2-nitro-phenyl)-penta-2,4 dien-1-one;
5-(2-Nitro-phenyl)-1-(4-pyridin-2-yl-piperazin-1-yl)-penta-2,4-dien-1-one;
1-(4-Cyclopentylmethyl-piperazin-1-yl)-5-(2-nitro-phenyl)-penta-2,4-dien-1-one;
5-(2-Nitro-phenyl)-1-(4-thiophen-3-ylmethyl-piperazin-1-yl)-penta-2,4 dien-1-one;
1-[4-(4-Fluoro-benzyl)-piperazin-1-yl]-5-(2-nitro-phenyl)-penta-2,4-dien-1-one;
1-(4-Butyl-piperazin-1-yl)-5-(2-nitro-phenyl)-penta-2,4-dien-1-one;
1-[4-(3-Chloro-phenyl)-piperazin-1-yl]-5-(2-nitro-phenyl)-penta-2,4-dien-1-one;
5-(2,6-Difluoro-phenyl)-1-(4-phenyl-piperazin-1-yl)-penta-2,4-dien-1-one;
1-(4-Cyclohexyl-piperazin-1-yl)-5-(2,6-difluoro-phenyl)-penta-2,4-dien-1-one;
1-[4-(3-Chloro-propyl)-piperazin-1-yl]-5-(2,6-difluoro-phenyl)-penta-2,4-dien-1-one;
1-(4-Cyclopentyl-piperazin-1-yl)-5-(2,6-difluoro-phenyl)-penta-2,4-dien-1-one;
5-(2,6-Difluoro-phenyl)-1-[4-(4-fluoro-benzyl)-piperazin-1-yl]-penta-2,4-dien-1-one;
1-(4-Cyclopentyl-piperazin-1-yl)-5-(2-fluoro-phenyl)-penta-2,4-dien-1-one;
1-(4-Cyclohexyl-piperazin-1-yl)-5-(2-fluoro-phenyl)-penta-2,4-dien-1-one;
5-(2-Fluoro-phenyl)-1-(4-pyridin-2-yl-piperazin-1-yl)-penta-2,4-dien-1-one;
5-(2-Fluoro-phenyl)-1-(4-phenyl-piperazin-1 -yl)-penta-2 4-dien-1 -one;
1-[4-(3-Chloro-propyl)-piperazin-1-yl]-5-(2-fluoro-phenyl)-penta-2,4-dien-1-one;
as well as therapeutically-acceptable salts thereof.

5. A method of preparation of compounds of general formula (I) according to claim 1, which comprises
condensation of an intermediate of general formula (II)

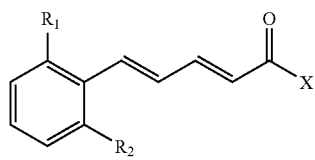

wherein $R_1$ and $R_2$ are defined as in the description of general formula (I) of claim 1, wherein X represents a leaving group or X represents hydroxyl, with an amine of general formula (III)

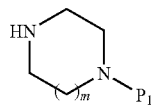

wherein $P_1$ represents a protective group, to yield an intermediate of general formula (IV),

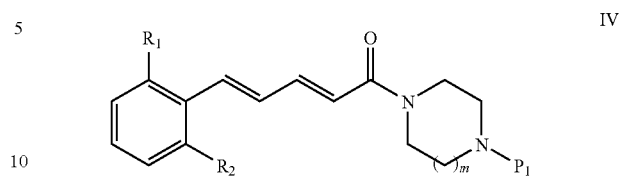

wherein $R_1$, $R_2$ and $P_1$ are defined as previously; and deprotection and reaction of the deprotected intermediate of general formula (IV) with a reagent of general formula $R_3(CH_2)_nY$, wherein $R_3$ and n are defined as in the description of general formula (I) of claim 1 and Y represents a leaving group, or with an aldehyde of formula $R_3$—$(CH_2)_{n-1}$—CHO wherein $R_3$ and n are defined as previously.

6. A method of preparation of compounds of general formula (I) according to claim 1, which comprises
condensation of an intermediate of general formula (II)

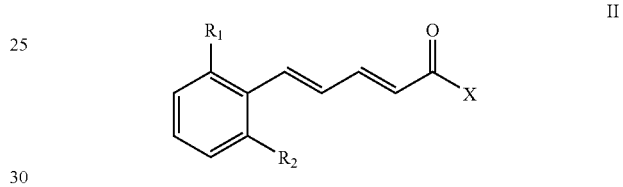

wherein $R_1$ and $R_2$ are defined as in the description of general formula (I) of claim 1 and X is a leaving group or hydroxyl, with an amine of general formula (V)

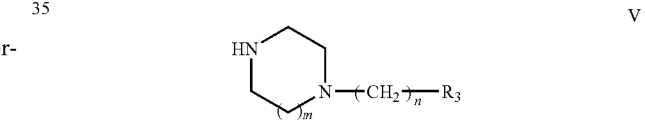

wherein m, n and $R_3$ are defined as in the description of general formula (I) of claim 1, yielding compounds of general formula (I).

7. The method according to claim 5, wherein X is chlorine.
8. The method according to claim 5, wherein Y is Cl, Br, I, $OSO_2CH_3$, $OSO_2CF_3$ or O-tosyl.
9. The method according to claim 6, wherein X is chlorine.
10. Pharmaceutical compositions containing as an active product at least one compound according to claim 1, in combination with a pharmaceutically-acceptable vehicle.
11. A composition comprising at least one compound according to claim 1 and another cardiovascular agent as a combination product, which is in the form of a simultaneous, separate or time-release formulation suitable for cardiovascular therapy.
12. The composition according to claim 11, wherein the other cardiovascular agent is an antiplatelet aggregation agent.
13. The composition according to claim 12 wherein the antiplatelet aggregation agent is aspirin, clopidogrel, ticlopidine, abciximab, tirofiban or eptifibatide.

* * * * *